(12) United States Patent
Turchetta et al.

(10) Patent No.: US 7,358,399 B2
(45) Date of Patent: Apr. 15, 2008

(54) PROCESS FOR THE PREPARATION OF N,N-DIISOPROPYL-3-(2-HYDROXY-5-METHYLPHENYL)-3-PHENYL-PROPANEAMINE

(75) Inventors: Stefano Turchetta, Patrica Fr (IT); Umberto Ciambecchini, Patrica Fr (IT); Pietro Massardo, Rome (IT)

(73) Assignee: Chemi SPA, Milan (IT)

( * ) Notice: Subject to any disclaimer, the term of this patent is extended or adjusted under 35 U.S.C. 154(b) by 174 days.

(21) Appl. No.: 11/244,396

(22) Filed: Oct. 6, 2005

(65) Prior Publication Data
US 2006/0079716 A1 Apr. 13, 2006

(30) Foreign Application Priority Data
Oct. 11, 2004 (IT) .......................... MI2004A1920

(51) Int. Cl.
C07C 209/22 (2006.01)
C07C 37/00 (2006.01)
(52) U.S. Cl. ...................... 564/395; 564/316; 568/731; 568/799
(58) Field of Classification Search ..................... None
See application file for complete search history.

(56) References Cited
U.S. PATENT DOCUMENTS
5,382,600 A * 1/1995 Jonsson et al. ............. 514/603
5,922,914 A * 7/1999 Gage et al. ................. 564/413

FOREIGN PATENT DOCUMENTS
WO    WO 01/49649 A1 *  7/2001
WO    WO 03/014060 A1 *  2/2003

OTHER PUBLICATIONS
Database CAPLUS on STN, Acc. No. 2005:41309, Listig et al., CZ 293791 (Jul. 14, 2004) (abstract).*

Database CASREACT on STN, Acc. No. 142:463446, Listig et al. CZ 293791 (Jul. 14, 2004) (abstract).*

* cited by examiner

Primary Examiner—Brian Davis
(74) Attorney, Agent, or Firm—Nixon & Vanderhye

(57) ABSTRACT

A process is described for the preparation of N,N-diisopropyl-3-(2-hydroxy-5-methylphenyl)-3-phenyl-propaneamine comprising substitution of the sulfonyloxy group of the compound of the formula

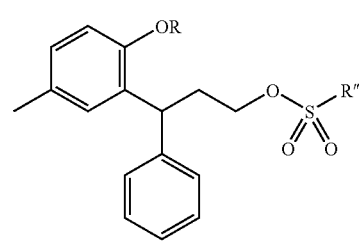

(V)

in which the substituents R and R" have the meanings stated in the description,
in a solvent comprising an ionic liquid,
to yield the tertiary amine of the formula

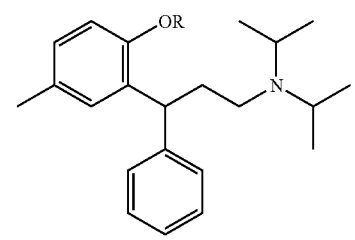

(VI)

and the subsequent deprotection thereof.

26 Claims, No Drawings

PROCESS FOR THE PREPARATION OF N,N-DIISOPROPYL-3-(2-HYDROXY-5-METHYLPHENYL)-3-PHENYL-PROPANEAMINE

This application is the claims priority to Italian Application No. MI2004A 001920, filed 11 Oct. 2004. The entire content of this application is incorporated herein by reference.

The present invention relates to a novel process for the preparation of N,N-diisopropyl-3-(2-hydroxy-5-methylphenyl)-3-phenyl-propaneamine.

PRIOR ART

N,N-Diisopropyl-3-(2-hydroxy-5-methylphenyl)-3-phenyl-propaneamine of the formula

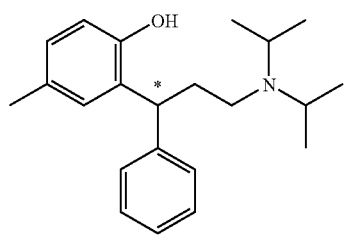
(I)

is a racemic compound which, when suitably resolved as R-(+)-N,N-diisopropyl-3-(2-hydroxy-5-methylphenyl)-3-phenyl-propaneamine L-tartrate, also known as tolterodine tartrate, of the formula

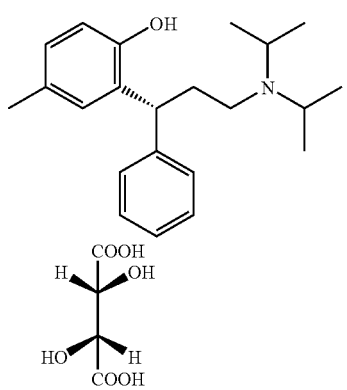
(Ia)

is commonly used in the treatment of acute urinary incontinence thanks to its muscarinic antagonist action.

U.S. Pat. No. 5,382,600 for the first time describes the compound and the analogues thereof, the use thereof as anticholinergics and the preparation thereof.

In the specific case of tolterodine (I), the synthesis starts from the reaction of 3,4-dihydro-6-methyl-4-phenyl-2H-benzopyran-2-one of the formula

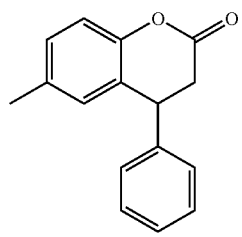
(II)

with methyl iodide and a base in hot methanol to yield the methyl-3-(2-methoxy-5-methylphenyl)-3-phenyl propionate of the formula

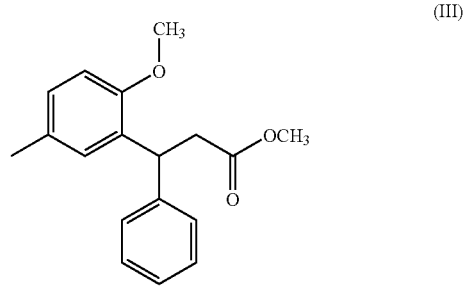
(III)

Then, the ester of the formula (III) is reduced with lithium aluminium hydride in diethyl ether to form the corresponding alcohol of the formula

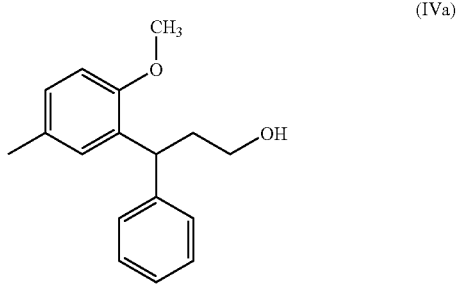
(IVa)

The alcohol (IVa) is subsequently activated with tosyl chloride and pyridine to yield the tosylate of the formula

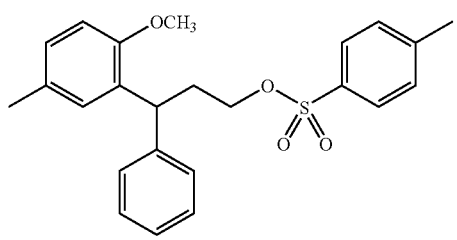

which, by substitution on the part of N,N-diisopropylamine in refluxing acetonitrile, is converted into the tertiary amine of the formula

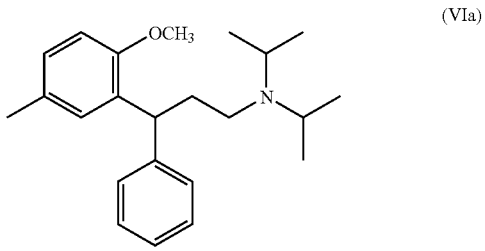
(VIa)

The demethylation step of the tertiary amine (VIa) with boron tribromide in dichloromethane leads to tolterodine as a racemic mixture (I), which is in turn resolved with L-(+)-tartaric acid to yield the compound R-(+)-tolterodine L-tartrate of the formula (Ia).

U.S. Pat. No. 5,382,600 also describes the alternative method illustrated in the following scheme:

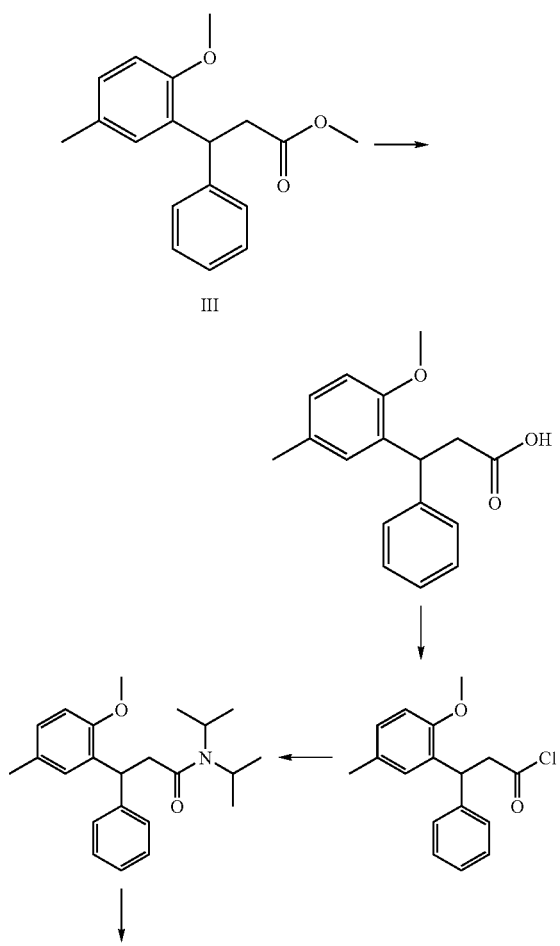

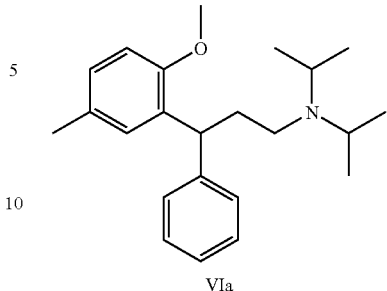

VIa comprising hydrolysis of the ester (III) with carboxylic acid, activation thereof as an acid chloride and subsequent conversion to the amide, followed by reduction with lithium aluminium hydride to obtain the protected tolterodine (VIa).

An alternative synthesis process for tolterodine tartrate has subsequently been described in U.S. Pat. No. 5,922,914 (Pharmacia & Upjohn Company) in which the dihydrocoumarin of the formula (II) is reduced with diisobutylaluminium hydride (DIBAL) in toluene at −20 to −25° C. into the corresponding 3,4-dihydro-6-methyl-4-phenyl-2H-1-benzopyran-2-ol of the formula

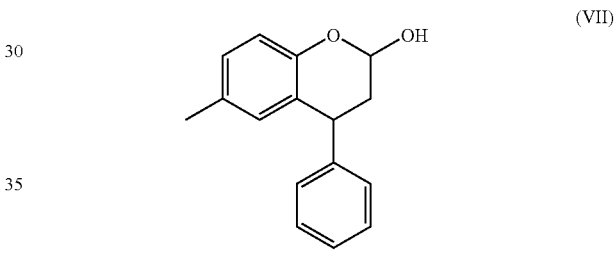

(VII)

Condensation of the compound (VII) with N,N-diisopropylamine in a hydrogen atmosphere in the presence of palladium on carbon leads to racemic tolterodine (I) which is resolved with L-(+)-tartaric acid to yield the compound R-(+)-tolterodine L-tartrate (Ia).

WO0149649, on the other hand, describes a process for the asymmetric synthesis of tolterodine, as shown in the following scheme:

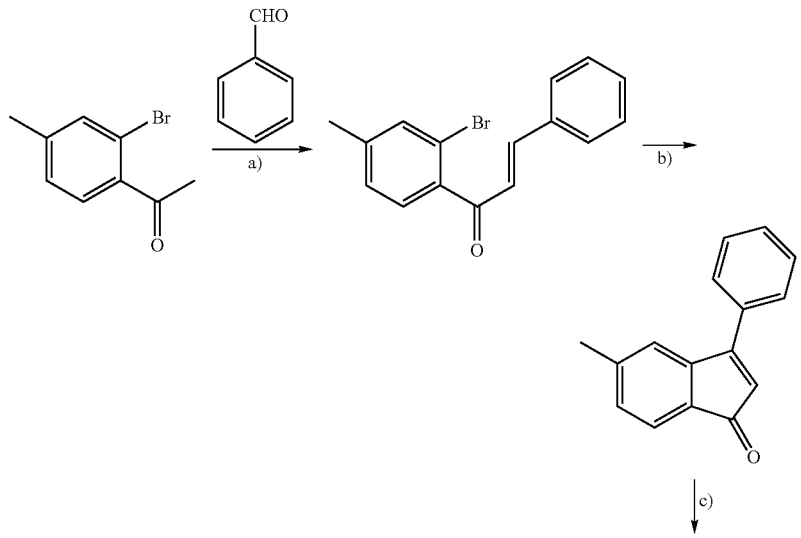

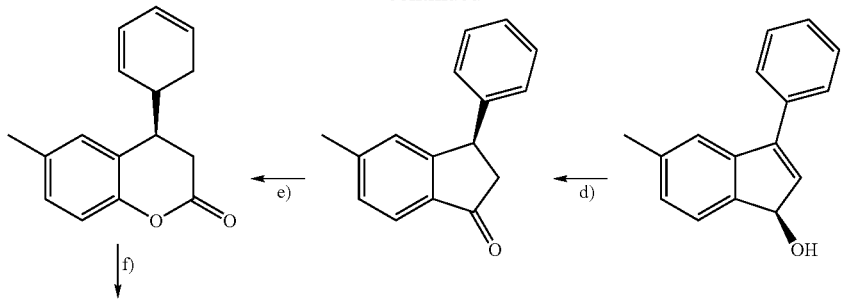

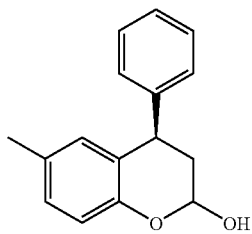

in which the final compound is obtained in the form of the single enantiomer (R), through the following steps:
a) condensation of acetophenone with benzaldehyde to yield the corresponding unsaturated compound;
b) intramolecular Heck alkylation to obtain the cyclopentenone compound;
c) enantiospecific reduction with optically active boranes to obtain the chiral alcohol;
d) isomerisation of the alcohol to obtain the ketone;
e) Bayer-Williger oxidation of the ketone to obtain the chromanone;
f) reduction of the chromanone to the hemiacetal;
g) subsequent synthetic working up of the hemiacetal to form tolterodine as described in U.S. Pat. No. 5,922,914.

WO03014060, on the other hand, describes an improved process for the synthesis of tolterodine, in which the first synthetic pathway described in U.S. Pat. No. 5,382,600 is substantially followed, using different reaction conditions in the following steps:
a. methylation reaction to obtain compound (III) starting from compound (II), performed with dimethyl sulfate instead of methyl iodide;
b. reduction reaction of compound (III) with sodium borohydride-aluminium chloride instead of lithium aluminium hydride;
c. demethylation of compound (VI) with HBr—AcOH instead of BBr$_3$.

In all the above-described cases, the use of costly and/or hazardous agents such as methyl iodide, lithium and aluminium hydride, diisobutylaluminium hydride, boron tribromide or dimethyl sulfate greatly limits the convenience and industrial applicability of these processes. Furthermore, in the synthetic pathways described in U.S. Pat. No. 5,382,600 and WO03014060, the substitution reaction by means of diisopropylamine on activated substrates such as tosylates or mesylates entails long reaction times, the necessity of working under pressure and in any case leads to modest yields making said process costly and somewhat unproductive.

The asymmetric synthetic pathway described in WO0149649 comprises a large number of steps and provides the use of costly catalysts and the borane-dimethyl sulfide complex, which is difficult to use industrially, during the reductive step (c), as well as diisobutylaluminium hydride, which is notoriously difficult to handle, for the reduction of the chromanone to the hemiacetal (step f).

As may accordingly be understood, there is still a very great need to identify economic and readily industrially applicable methods for synthesising tolterodine. We have surprisingly found a novel process for the synthesis of tolterodine of the formula (I), preferably of the L-tartrate (Ia) thereof, by means of a pathway which can be implemented on a large scale, uses readily commercially available reactants, which are non-toxic and easily handled, and leads to a high purity product and in elevated yields.

SUMMARY OF THE INVENTION

The present invention accordingly provides a process for the preparation of racemic tolterodine (I) and the pharmaceutically acceptable salts thereof, preferably R-(+)-tolterodine L-tartrate (Ia), comprising:
1) reduction of the dihydrocoumarin of the formula

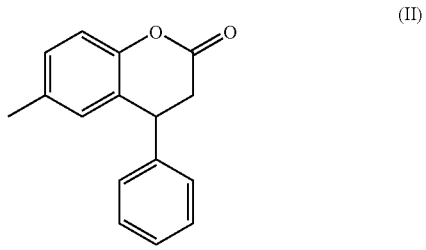

(II)

with a borohydride to yield 3-(2-hydroxy-5-methylphenyl)-3-phenylpropanol of the formula

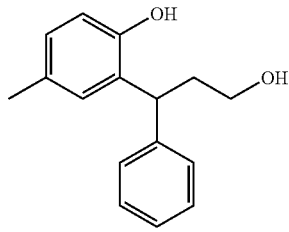
(VIII)

2) protection of the phenolic hydroxyl group with a suitable protective group to obtain the compound of the formula

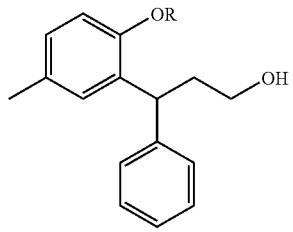
(IV)

in which
R represents $C_1$-$C_6$ alkyl, $CH_2$—Ar, or $SiR'_3$, in which Ar represents optionally substituted aryl and each R' may mutually independently be linear or branched alkyl or optionally substituted aryl, or acyl
3) activation of the primary hydroxyl group by means of reaction with optionally substituted aryl or alkyl-sulfonyl halides to yield the compounds of the formula

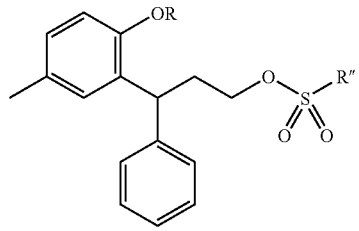
(V)

in which R has the above-stated meaning and R" represents $C_1$-$C_6$ alkyl or optionally substituted aryl;
4) substitution of the sulfonyloxy group with N,N-diisopropylamine in a solvent comprising an ionic liquid to yield the tertiary amine of the formula

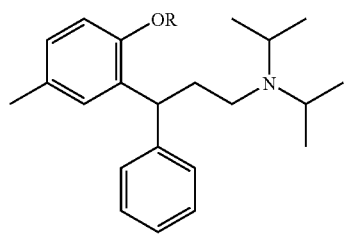
(VI)

in which R has the above-stated meanings;

5) deprotection of the OR group to yield tolterodine as a racemic mixture of the formula

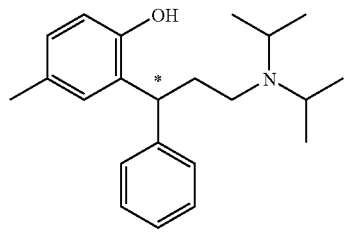
(I)

and, optionally, salification thereof with a pharmaceutically acceptable acid, and preferably
6) resolution of the racemic tolterodine (I) with L-(+)-tartaric acid to yield the compound R-(+)-tolterodine L-tartrate of the formula

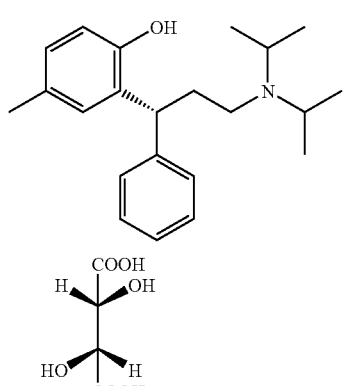
(Ia)

DETAILED DESCRIPTION OF THE INVENTION

The process provided by the present invention is characterised in particular by synthesis steps 1) and 4).

With regard to synthesis step 1), it has unexpectedly been found that alkali and alkaline earth metal borohydrides, and in particular sodium borohydride, in a linear or branched aliphatic alcoholic solvent, preferably selected from among methanol, ethanol and isopropanol, are capable of reducing the dihydrocoumarin (II) to form the alcohol (VIII) at elevated yields and using a simple synthetic method.

Said borohydride, preferably sodium borohydride, is used in a molar ratio of between 0.5 and 2.5, preferably around 1.5, per mole of substrate to be reduced of the formula (II).

The diol (VIII) is then selectively protected in synthesis step 2), by derivatising the phenolic hydroxyl group with alkylating agents, such as methyl iodide, dimethyl sulfate, methanol tosylate or benzyl bromide, or silylating agents, such as trimethylchlorosilane, or other protective groups suitable for obtaining derivatives of the type (IV), in accordance with phenol protection methods familiar to the person skilled in the art, such as those described for example in T. W. Green, P. G. M. Wuts, Protective groups in organic synthesis, $2^{nd}$ edition, John Wiley & Sons 1991. In a preferred embodiment of the process according to the present invention, R is methyl or benzyl.

The reduction of the dihydrocoumarin (II) to the diol (VIII) has never previously been described in the literature nor likewise has the diol intermediate (VIII).

In the literature, in order to obtain the intermediate (IV), the -dihydrocoumarin (II) is reacted under basic conditions, while simultaneously derivatising it with alkylating agents (such as methyl iodide or benzyl bromide) in order to obtain the intermediate (III) which is subsequently reduced to the alcohol (IV) by using lithium aluminium hydride or sodium borohydride coupled with Lewis acids such as $AlCl_3$ and the like.

The synthesis method provided by the present invention thus makes it possible to obtain the alcohol (VI) from the dihydrocoumarin (II) with the same number of steps as in the prior art, but avoiding the use of reactants such as $LiAlH_4$ or $AlCl_3$, which are problematic to use given their elevated reactivity and moisture instability, and the evolution in the reaction medium of gases which are hazardous to safety, such as diborane, when processing $NaBH_4$ and $AlCl_3$.

Step 3) of the present process, namely activation of the primary hydroxyl group by means of reaction with optionally substituted aryl or alkyl-sulfonyl halides to yield the compounds of the formula (V) is generally performed under conventional conditions, for example as described in U.S. Pat. No. 5,382,600.

In a preferred embodiment of the process according to the present invention, R" is p-tolyl or mesyl.

As already stated, the substitution step described in point 4) is another characterising aspect of the process provided by the present invention.

As may be learnt from the prior art, introducing the diisopropylamine functional group into substrates of the formula (V) is difficult to carry out.

It is usually performed by a nucleophilic substitution reaction on activated substrates of the type (V) by means of diisopropylamine in solvents such as acetonitrile. The results which are obtained after 4 to 6 days of refluxing reaction are always modest from the standpoint of yield (69%, U.S. Pat. No. 5,382,600 Example 5c), and, if more acceptable values are to be achieved (WO03014060 reports a yield of 78%), more highly energetic experimental conditions are required, such as elevated reaction pressures in order to obtain higher temperatures than the reflux temperature of the reaction mixture, and reaction times of 50 to 55 hours, with complications from the standpoint of industrial applicability and safety.

Conversely, it has surprisingly been found that, by performing the nucleophilic substitution reaction of step 4) in solvents comprising ionic liquids (IL), elevated yields are obtained in shorter times without having to resort to reactions performed under pressure.

The ionic liquids consist of molecules of an ionic nature typically composed of asymmetric organic cations such as imidazolium, pyridinium, piperidinium, tetraalkylammonium, tetraalkylphosphonium and of inorganic or organic anions, as shown below:

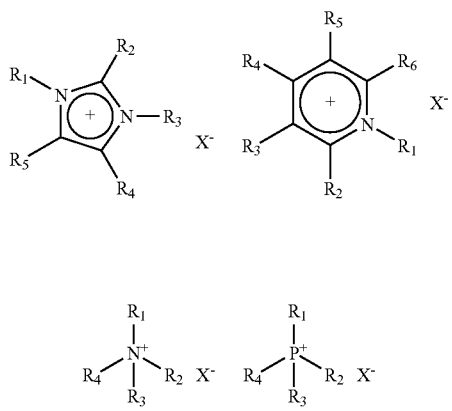

in which $R_1$, $R_2$, $R_3$, $R_4$, $R_5$, $R_6$ may independently be H, linear or branched $C_1$-$C_6$ alkyl, optionally substituted aryl and X represents an anion selected from among $Cl^-/AlCl_3$, $Cl^-$, $Br^-$, $I^-$, $NO_3^-$, $SO_4^{--}$, $CF_3COO^-$, $CF_3SO_2^-$, $BF_4^-$, $PF_6^-$, $[(CF_3SO_2)_2N]^-$.

Such compounds are often liquid over a wide temperature range (Room Temperature Ionic Liquids, "RTILs") and are thermally stable (T>200° C.). They do not have a measurable vapour pressure and are excellent solvating agents for organic and inorganic compounds and for polymers. Their characteristics of non-volatility, non-flammability, thermal stability, recyclability and non-toxicity to the environment, combined with simple and low cost production methods, make ionic liquids ideal candidates for the replacement of volatile organic compounds (VOCs), which have traditionally been used as solvents in industry.

The ionic liquids used in the synthesis step from (V) to (VI), are for example those stated above, with preferably used ionic liquids being those having alkyl-imidazolium or alkyl-pyridinium as the cations, of the formula

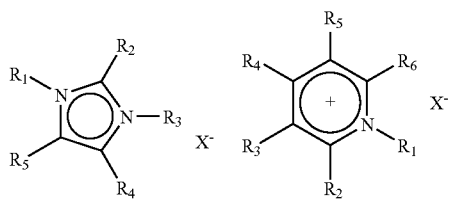

and, more preferably among the N-methyl-alkyl-imidazolium or N-alkyl-pyridinium compounds, those which are not substituted on the carbon atoms. The anion X is preferably selected from among tetrafluoroborate and hexafluorophosphate.

Such solvents make it possible, with reaction times of approx. 30 hours at the reflux temperature of the mixture, to obtain (VI) from (V) with yields generally of greater than 80%, according to the synthesis scheme shown below

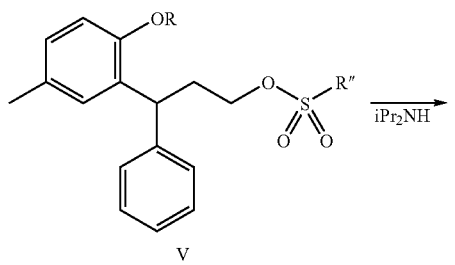

in which R and R" have the meanings already explained above.

In a preferred embodiment of the process according to the present invention, said substitution of the sulfonyloxy group of the compound of the formula (V) with N,N-diisopropylamine is performed at a temperature of between 20 and 100° C., preferably between 80 and 90° C.

The reaction product (VI) of said substitution of the sulfonyloxy group of the compound of the formula (V) with N,N-diisopropylamine is extracted from the mixture with an organic solvent selected from among esters, ethers, ketones, nitrites and aliphatic or aromatic hydrocarbons, preferably with an ether.

According to step 5 of the process provided by the present invention, the protective group R of (VI) may then be removed using suitable methods known from the literature (T. W. Green, P. G. M. Wuts, Protective groups in organic synthesis, 2nd edition, John Wiley & Sons 1991) and the racemic tolterodine base (I) obtained, for example by using concentrated refluxing HBr or refluxing mixtures thereof with acetic acid or by using $AlCl_3$ or $PBr_3$.

The racemic tolterodine base (I) may then be transformed into R-(+)-tolterodine L-tartrate (Ia), again according to methods known from the literature, for example as described U.S. Pat. No. 5,382,600.

In one particularly preferred embodiment of the process provided by the present invention, the dihydrocoumarin (II) is reduced by means of sodium borohydride in isopropanol at ambient temperature and the alcohol (VIII) derived therefrom is isolated by crystallisation.

The alcohol (VIII) is then subjected to derivatisation of the phenolic hydroxyl group, which may be performed by benzylation by means of benzyl chloride in a biphasic water-NaOH and toluene reaction medium with the assistance of a phase-transfer agent (generally tetrabutylammonium bromide), or by methylation with methyl iodide and sodium carbonate in acetone. The resultant alcohol (IV) is then derivatised on the hydroxyl group by means of functionalisation with mesyl chloride or tosyl chloride in toluene in the presence of a base such as triethylamine. The reaction gives rise to the compound (V) which is subjected to a substitution reaction with diisopropylamine in a refluxing ionic liquid, for example N-methyl-N-hexyl-imidazolium tetrafluoroborate, to obtain (VI). The compound (VI) is subsequently transformed into tolterodine by removal of the hydroxyl protection performed with HBr in a 48% strength refluxing aqueous solution, in the event that it is the compound (VIa), or by catalytic hydrogenation in the event that R is benzyl.

The following Examples are intended to illustrate the invention in greater detail, but without limiting it in any way.

EXAMPLE 1

Preparation of
3-(2-hydroxy-5-methylphenyl)-3-phenylpropanol
(VIII)

A basic aqueous solution of sodium borohydride prepared beforehand by dissolving 23.8 g (0.630 moles) of $NaBH_4$ at ambient temperature in 170 ml of $H_2O$ and 3.5 ml of 30% wt./vol. NaOH was added dropwise to a suspension of 3,4-dihydro-6-methyl-4-phenyl-2H-benzopyran-2-one of the formula (II) (100 g, 0.420 moles) in isopropanol (200 ml). Once addition was complete, the temperature was adjusted to 60° C. and the course of the reaction was monitored by TLC (eluent: cyclohexane/acetone: 70/30) until the substrate had completely disappeared. After 5 h, the reaction mixture was cooled to ambient temperature and HCl (2N) was added until a final pH of 7.0 was obtained. Stirring was continued for 30 min at ambient temperature, then the resultant suspension was filtered through a Buchner filter. The filtered solution was concentrated under reduced pressure and the crude residue was crystallised from toluene (280 ml) to yield 87.4 g (yield 86%) of 3-(2-hydroxy-5-methylphenyl)-3-phenylpropanol (VIII) as a white solid.

EXAMPLE 2

Preparation of
3-(2-benzyloxy-5-methylphenyl)-3-phenylpropanol
(IV, R=benzyl)

80 ml of an aqueous solution of NaOH (30% wt./vol.) and 10.6 g (0.033 moles) of tetrabutylammonium bromide (TBABr) were added to a suspension of 3-(2-hydroxy-5-methylphenyl)-3-phenylpropanol of the formula (VIII) (80 g, 0.330 moles) in toluene (320 ml). The internal temperature was adjusted to 50° C., 45.5 ml (0.396 moles) of benzyl chloride were added dropwise in approx. 1 h and the course of the reaction was monitored by means of TLC (eluent: cyclohexane/acetone: 70/30) until the substrate had completely disappeared. After 7 h, the reaction mixture was cooled to ambient temperature and the aqueous phase was removed. The organic phase was washed with water (3×100 ml), was then evaporated under a vacuum to remove the solvent and to obtain 104 g of 3-(2-benzyloxy-5-methylphenyl)-3-phenylpropanol (IV) as a yellow-brown oil (yield 96%).

EXAMPLE 3

Preparation of 3-(2-benzyloxy-5-methylphenyl)-3-phenylpropyl-p-toluene-sulfonate (V, R=benzyl, R"=p-tolyl)

The propanol of the formula (IV) (90 g, 0.272 moles) was dissolved in methylene chloride (300 ml).

The solution was cooled to 0° C. and triethylamine (41.2 g, 0.408 moles) and p-toluenesulfonyl chloride (56.8 g, 0.299 moles) were added in quick succession. The reaction mixture was left to stand at ambient temperature for 20 h, then cooled to 0° C. and water (200 ml) and dilute HCl (2N) (100 ml) were added. The organic phase was separated and washed with water (2×100 ml). The solvent was removed under reduced pressure to yield 121 g of 3-(2-benzyloxy-5-methylphenyl)-3-phenylpropyl-toluene-sulfonyl (V) as yellow-brown oil (yield 92%).

EXAMPLE 4

Preparation of N,N-diisopropyl-3-(2-benzyloxy-5-methylphenyl)-3-phenyl-propylamine (VI, R=benzyl)

The tosylate of the formula (V) (100 g, 0.206 moles) was heated to 80° C. in the presence of hexylmethylimidazolium tetrafluoroborate [Hexmim].BF4 (250 ml) and N,N-diisopropylamine (210 g, 2.06 moles) for 30 h. The temperature was adjusted to 50° C., stirring was stopped, then the mixture was left to settle for 15 minutes. The lower phase, with a high ionic liquid content, was separated and extracted with methyl tert.-butyl ether (MTBE) (3×200 ml) at 50° C. The upper phase, with a high N,N-diisopropylamine content, was distilled at 80-82° C. until an oily residue was obtained. The organic phases (MTBE) were added at 25° C. to the crude distillation product and then washed with water (100 ml) and dilute soda (2N) (100 ml) and extracted with dilute HCl (2N) (2×200 ml). The acidic aqueous phases were washed with MTBE (2×50 ml) then adjusted to a basic pH (10-11) with dilute soda (10% wt./vol.). The basic aqueous phases were extracted with MTBE (3×100 ml). The combined organic phases were evaporated to yield 70.8 g of N,N-diisopropyl-3-(2-benzyloxy-5-methylphenyl)-3-phenylpropylamine of the formula (VI) (yield 83%).

EXAMPLE 5

Preparation of N,N-diisopropyl-3-(2-benzyloxy-5-methylphenyl)-3-phenyl-propylamine (VI, R=benzyl)

The tosylate of the formula (V) (50 g, 0.103 mol) was heated to 80° C. in the presence of butylmethylimidazolium tetrafluoroborate [Bmim]BF4 (125 ml) and N,N-diisopropylamine (105 g, 1.03 moles) for 26 h. The temperature was adjusted to 50° C., stirring was stopped, then the mixture was left to settle for 15 minutes. The lower phase, with a high ionic liquid content, was separated and extracted with methyl tert.-butyl ether (MTBE) (3×100 ml) at 50° C. The upper phase, with a high N,N-diisopropylamine content, was distilled at 80-82° C. until an oily residue was obtained. The organic phases (MTBE) were added at 25° C. to the crude distillation product and then washed with water (100 ml) and dilute soda (2N) (50 ml) and extracted with dilute HCl (2N) (2×100 ml). The acidic aqueous phases were washed with MTBE (2×50 ml) then adjusted to a basic pH (10-11) with dilute soda (10% wt./vol.). The basic aqueous phases were extracted with MTBE (2×100 ml). The combined organic phases were evaporated to yield 27.3 g of N,N-diisopropyl-3-(2-benzyloxy-5-methylphenyl)-3-phenylpropylamine of the formula (VI) (yield 64%).

EXAMPLE 6

Preparation of 3-(2-methoxy-5-methylphenyl)-3-phenylpropyl-methanesulfonate (V, R=CH$_3$)

The propanol of the formula (IV) (R=Me) (20 g, 0.083 moles) was dissolved in methylene chloride (300 ml).

The solution was cooled to 0° C. and triethylamine (12.5 g, 0.124 moles) and methanesulfonyl chloride (10.3 g, 0.091 moles) were added in quick succession. The reaction mixture was left to stand at ambient temperature for 20 h, then cooled to 0° C. and water (200 ml) and dilute HCl (2N) (100 ml) were added. The organic phase was separated and washed with water (2×100 ml). The solvent was removed under reduced pressure and the crude product crystallised from MTBE (150 ml) to yield 23.9 g of 3-(2-methoxy-5-methylphenyl)-3-phenylpropyl-methanesulfonate (V) as a white solid (yield 90%).

EXAMPLE 7

Preparation of N,N-diisopropyl-3-(2-methoxy-5-methylphenyl)-3-phenyl-propylamine (VI, R=CH$_3$)

The mesylate of the formula V (R=CH$_3$), as prepared in Example 6 (20 g, 0.062 moles) was heated to 80° C. in the presence of hexylmethylimidazolium tetrafluoroborate [Hexmim]BF4 (50 ml) and N,N-diisopropylamine (62 g, 0.62 moles) for 24 h. The temperature was adjusted to 50° C., stirring was stopped, then the mixture was left to settle for 15 minutes. The lower phase, with a high ionic liquid content, was separated and extracted with methyl tert.-butyl ether (MTBE) (3×50 ml) at 50° C. The upper phase, with a high N,N-diisopropylamine content, was distilled at 80-82° C. until an oily residue was obtained. The organic phases (MTBE) were added at 25° C. to the crude distillation product and then washed with water (50 ml) and dilute soda (2N) (50 ml) and extracted with dilute HCl (2N) (2×50 ml). The acidic aqueous phases were washed with MTBE (2×25 ml) then adjusted to a basic pH (10-11) with dilute soda (10% wt./vol.). The basic aqueous phases were extracted with MTBE (2×50 ml). The combined organic phases were evaporated to yield 12.6 g of N,N-diisopropyl-3-(2-methoxy-5-methylphenyl)-3-phenylpropylamine of the formula (VI) (yield 63%).

What is claimed is:
1. A process for the preparation of racemic tolterodine of the formula

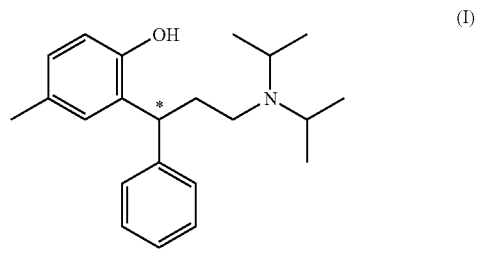

(I)

and the pharmaceutically acceptable salts thereof, comprising:
substitution of the sulfonyloxy group of the compound of the formula

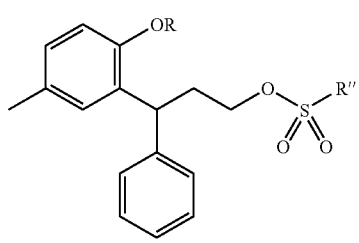

(V)

in which
R represents $C_1$-$C_6$ alkyl, $CH_2$—Ar, $SiR'_3$,
in which Ar represents optionally substituted aryl and each R' may mutually independently be linear or branched alkyl or optionally substituted aryl, or acyl and
R" represents $C_1$-$C_6$ alkyl or optionally substituted aryl,
with N,N-diisopropylamine in a solvent comprising an ionic liquid to yield the tertiary amine of the formula

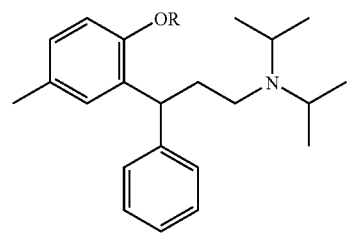

(VI)

in which R has the above-stated meanings,
subsequent deprotection of the OR group to yield racemic tolterodine of the formula

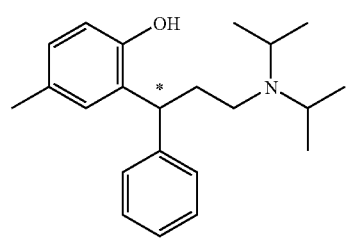

(I)

and optionally,
salification thereof with a pharmaceutically acceptable acid.

2. A process according to claim 1 further comprising reduction of the dihydrocoumarin of the formula

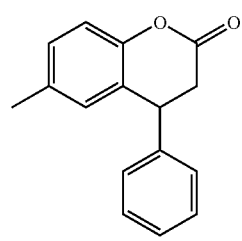

(II)

with a borohydride to yield 3-(2-hydroxy-5-methylphenyl)-3-phenylpropanol of the formula

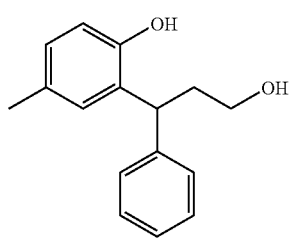

(VIII)

protection of the phenolic hydroxyl group with a suitable protective group, to yield the compound of the formula

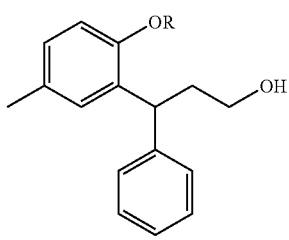

(IV)

in which R has the above-stated meanings, and
activation of the primary hydroxyl group of the compound IV by reaction with optionally substituted aryl or alkyl-sulfonyl halides to yield the compounds of the formula

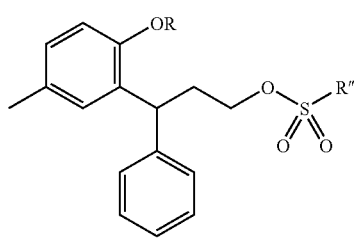

(V)

in which R has the above-stated meaning and R" represents $C_1$-$C_6$ alkyl or optionally substituted aryl.

3. A process for the preparation of R-(+)-tolterodine L-tartrate of the formula

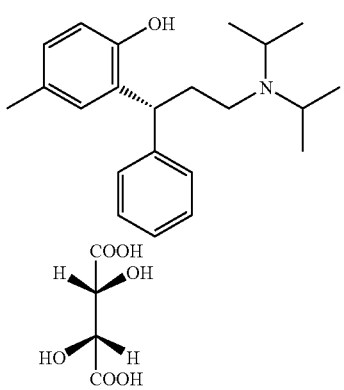

(Ia)

which comprises resolution of the racemic tolterodine (I), prepared according to the process of claim 1, with L-(+)-tartaric acid.

4. The process according to claim 2 in which said reduction of the dihydrocoumarin II is performed by using an alkali metal borohydride.

5. The process according to claim 4 in which said borohydride, is used in a molar ratio of between 0.5 and 2.5 per mole of substrate to be reduced of the formula (II).

6. The process according to claim 4 in which said reduction is performed in a solvent selected from the group consisting of linear and branched aliphatic alcohols.

7. The process according to claim 1 in which said ionic liquid is a compound of the formula

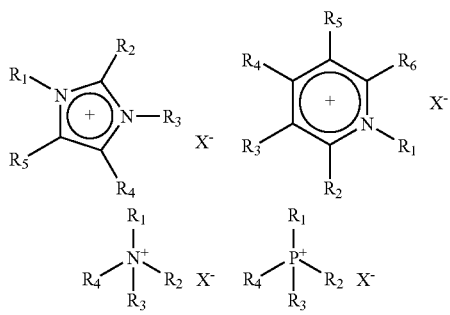

in which $R_1$, $R_2$, $R_3$, $R_4$, $R_5$, $R_6$ may independently be H, linear or branched $C_1$-$C_6$ alkyl, optionally substituted aryl and X represents an anion selected from the group consisting of $Cl^-AlCl_3$, $Cl^-$, $Br^-$, $I^-$, $NO_3^-$, $SO_4^{--}$, $CF_3COO^-$, $CF_3SO_2^-$, $BF_4^-$, $PF_6^-$, and $[(CF_3SO_2)_2N]^-$.

8. The process according to claim 7 in which said ionic liquid is a compound of the formula

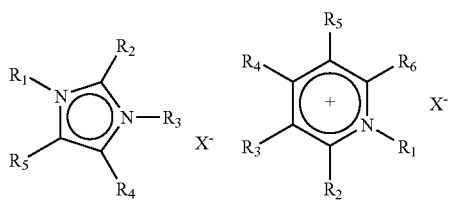

wherein $R_1$, $R_2$, $R_3$, $R_4$, $R_5$, $R_6$ and X are as defined in claim 7.

9. The process according to claim 7 in which said anion X is selected from the group consisting of tetrafluoroborate and hexafluorophosphate.

10. The process according to claim 1 in which R is methyl or benzyl.

11. The process according to claim 1 in which R" is p-tolyl or mesyl.

12. The process according to claim 1 in which said substitution of the sulfonyloxy group of the compound of the formula (V) with N,N-diisopropylamine is performed at a temperature of between 20 and 100° C.

13. The process according to claim 1, in which the reaction product (VI) of said substitution of the sulfonyloxy group of the compound of the formula (V) with N,N-diisopropylamine is extracted from the mixture with an organic solvent selected from the group consisting of esters, ethers, ketones, nitriles, aliphatic hydrocarbons and aromatic hydrocarbons.

14. A process for the preparation of the compound of the formula

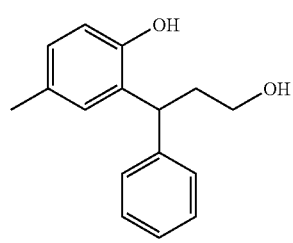

which comprises reduction of the dihydrocoumarin of the formula

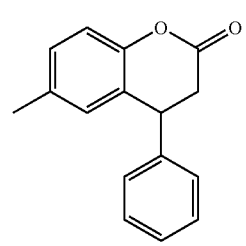

with a borohydride.

15. The process according to claim 14 in which said borohydride is an alkali metal borohydride.

16. The process according to claim 14 in which said borohydride, is used in a molar ratio of between 0.5 and 2.5 per mole of substrate to be reduced of the formula (II).

17. The process according to claim 14, in which said reduction is performed in a solvent selected from the group consisting of linear and branched aliphatic alcohols.

18. The process according to claim 4 in which said reduction of the dihydrocoumarin II is performed by using sodium borohydride.

19. The process according to claim 5 in which said borohydride is used in a molar ratio of about 1.5 per mole of substrate to be reduced of the formula (II).

20. The process according to claim 6 in which said reduction is performed in a solvent selected from the group consisting of methanol, ethanol and isopropanol.

21. The process according to claim 8, wherein the compound is selected from the group consisting of N-methyl-alkyl-imidazolium and N-alkyl pyridinium compounds which are not substituted on the carbon atoms.

22. The process according to claim 12 in which said substitution of the sulfonyloxy group of the compound of the formula (V) with N,N-diisopropylamine is performed at a temperature of between 80 and 90° C.

23. The process according to claim 13, in which the organic solvent is an ether.

24. The process according to claim 15 in which said borohydride is sodium borohydride.

25. The process according to claim 16 in which said borohydride is used in a molar ratio of about 1.5 per mole of substrate to be reduced of the formula (II).

26. The process according to claim 17, in which said reduction is performed in a solvent selected from the group consisting of methanol, ethanol and isopropanol.

* * * * *